(12) United States Patent
Hayashi

(10) Patent No.: US 6,254,544 B1
(45) Date of Patent: Jul. 3, 2001

(54) HEART-FUNCTION MONITOR APPARATUS

(75) Inventor: Kazuko Hayashi, Kyoto (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/575,822

(22) Filed: May 22, 2000

(30) Foreign Application Priority Data

May 25, 1999 (JP) ................................. 11-145502

(51) Int. Cl.$^7$ ....................................... A61B 5/02
(52) U.S. Cl. ........................................ 600/500; 606/485
(58) Field of Search ....................... 600/500, 490, 600/485, 526, 504, 561, 586

(56) References Cited

U.S. PATENT DOCUMENTS 5,810,011 * 9/1998 Kunig ................................. 128/668
5,921,936 * 7/1999 Inukai et al. ......................... 600/490

* cited by examiner

*Primary Examiner*—Robert L. Nasser
*Assistant Examiner*—Patricia C. Mallari
(74) *Attorney, Agent, or Firm*—Oliff & Berridge, PLC

(57) ABSTRACT

An apparatus for monitoring a function of a heart of a person, including a pre-ejection period measuring device which non-invasively measures a pre-ejection period, an ejection-period measuring device which non-invasively measures an ejection period, an aorta-pressure estimating device for estimating a blood pressure in an aorta of the subject, a telediastolic-aorta-pressure determining device for determining, based on an aorta blood pressure estimated by the aorta-pressure estimating device, a telediastolic blood pressure in the aorta at a telediastolic time of the heart, a telesystolic-aorta-pressure determining device for determining, based on an aorta blood pressure estimated by the aorta-pressure estimating device, a telesystolic blood pressure in the aorta at a telesystolic time of the heart, and a cardiac-mechanical-efficiency determining device for determining, based on the measured pre-ejection period, the measured ejection period, the determined telediastolic aorta blood pressure, and the determined telesystolic aorta blood pressure, a cardiac mechanical efficiency of the person according a predetermined relationship between (A) cardiac mechanical efficiency and (B) (b1) pre-ejection period, (b2) ejection period, (b3) telediastolic aorta blood pressure, and (b4) telesystolic aorta blood pressure.

15 Claims, 11 Drawing Sheets

HEART-FUNCTION MONITOR APPARATUS

BACKGROUND OF THE INVENTION

1. Field of the Invention

The present invention relates to a heart-function monitor apparatus which monitors a function of the heart of a living subject by evaluating a cardiac mechanical efficiency, i.e., a mechanical efficiency of the heart.

2. Related Art Statement

When a characteristic of the left ventricle of the heart as an elastic tube, that is, an elastic coefficient of the same, at a telesystolic time immediately before the aortic valve is closed, is defined as a left-ventricle telesystolic elastance $E_{es}$, and a characteristic of the aorta as an effective elastic tube, that is, an elastic coefficient of the aorta is defined as an aorta effective elastance $E_a$, the ratio, $E_{es}/E_a$, of the left-ventricle telesystolic elastance $E_{es}$ to the aorta effective elastance $E_a$ indicates a degree of balance of the connection of the left ventricle and the aorta, that is, a mechanical efficiency of the left ventricle. Accordingly, this ratio $E_{es}/E_a$ can be used as an important index of the function of the heart. It has been theoretically and experimentally elucidated that the ratio $E_{es}/E_a$ changes depending upon the current state of the cardiac function, such as at rest, under stress, or in heart failure, and that the ratio $E_{es}/E_a$ reflects cardiac metabolic rate (i.e., the ratio of the amount of work of the heart to the amount of consumption of oxygen by the cardiac muscle).

However, determination of the above left-ventricle telesystolic elastance $E_{es}$, which is also known as the maximum pressure-volume ratio, or the left-ventricle telesystolic pressure-volume ratio, needs (a) detecting continuously respective changes of the inner pressure and inner volume of the left ventricle, (b) obtaining, in a two-dimensional coordinate system having a volume axis indicative of the inner volume of the left ventricle and a pressure axis indicative of the inner pressure of the same, a plurality of pressure-volume loops before and after preload or afterload is applied to the cardiac muscle, (c) estimating, based on the plurality of pressure-volume loops, a left-ventricle unstressed volume, $V_0$, taken when the inner pressure would take zero, and (d) determining the telesystolic elastance $E_{es}$ by dividing a telesystolic pressure, $P_{es}$, by the difference of a telesystolic volume, $V_{es}$, and the unstressed volume $V_0$. Thus, the determination of the telesystolic elastance $E_{es}$ needs measuring simultaneously the inner pressure and inner volume of the left ventricle. Conventionally, this determination has been carried out by an invasive method in which a cutting operation or a catheter insertion is employed. Thus, it has been very difficult to monitor the cardiac function. In addition, determination of the aorta effective elastance $E_a$ needs (e) determining, in the above-indicated two-dimensional coordinate system, the effective elastance $E_a$ by dividing the telesystolic pressure $P_{es}$ by the difference of a telediastolic volume, $V_{ed}$, and the telesystolic volume $V_{es}$. Thus, conventionally, this determination also needs measuring invasively the inner pressure and inner volume of the left ventricle, and it has been very difficult to monitor the cardiac function.

SUMMARY OF THE INVENTION

It is therefore an object of the present invention to provide a heart-function monitor apparatus which can non-invasively and easily monitor a cardiac mechanical efficiency $E_{es}/E_a$ of a living subject.

The Inventor has carried out extensive studies in the above-mentioned background, and has found the fact that when (a) a pressure-volume ratio, i.e., an elastance, E(t), is obtained by dividing a continuously obtained left-ventricle inner pressure, P(t), by the difference, (V(t)–$V_0$), of a continuously obtained left-ventricle inner volume, V(t), and the above-indicated unstressed volume $V_0$, (b) a time-elastance curve is drawn, as shown in FIG. 8, in a two-dimensional coordinate system having a time axis and an elastance axis, (c) a first portion of a length of the time-elastance curve between its start end and a maximum elastance, $E_{max}$, i.e., a telesystolic elastance $E_{es}$ (the first portion corresponds to a pre-ejection period, PEP) is approximated by a straight line, $L_1$, as shown in FIG. 9, and a second portion of the length (the second portion corresponds to an ejection period, ET) is approximated by a straight line, $L_2$, and (d) k is defined to be equal to the ratio, $k_2/k_1$, of a slope, $k_2$, of the straight line $L_2$ to a slope, $k_1$, of the straight line $L_1$, the ratio of the left-ventricle telesystolic elastance $E_{es}$ to the aorta effective elastance $E_a$, i.e., the cardiac mechanical efficiency $E_{es}/E_a$ can be expressed by using a telediastolic aorta (blood) pressure, $P_{ad}$, i.e., an aorta inner pressure at the telediastolic time of the left ventricle; a telesystolic aorta pressure $P_{es}$, i.e., an aorta inner pressure at the telesystolic time of the left ventricle; the ejection period ET and the pre-ejection period PEP of the left ventricle; and the ratio k. The present invention has been developed based on this finding.

(1) According to a first feature of the present invention, there is provided an apparatus for monitoring a function of a heart of a living subject, comprising a pre-ejection period measuring device which non-invasively measures a pre-ejection period from a time when contraction of a cardiac muscle of a left ventricle of the heart starts, to a time when ejection of blood from the left ventricle starts; an ejection-period measuring device which non-invasively measures an ejection period during which the blood is ejected from the left ventricle; an aorta-pressure estimating means for estimating blood pressure values in an aorta of the subject; a telediastolic-aorta-pressure determining means for determining, based on the aorta blood pressure values estimated by the aorta-pressure estimating means, a telediastolic blood pressure in the aorta at a telediastolic time of the heart; a telesystolic-aorta-pressure determining means for determining, based on the aorta blood pressure values estimated by the aorta-pressure estimating means, a telesystolic blood pressure in the aorta at a telesystolic time of the heart; and a cardiac-mechanical-efficiency determining means for determining, based on the measured pre-ejection period, the measured ejection period, the determined telediastolic aorta blood pressure, and the determined telesystolic aorta blood pressure, a cardiac mechanical efficiency of the subject according a predetermined relationship between (A) cardiac mechanical efficiency and (B) (b1) pre-ejection period, (b2) ejection period, (b3) telediastolic aorta blood pressure and (b4) telesystolic aorta blood pressure.

According to this feature, the cardiac-mechanical-efficiency determining means determines, based on the non-invasively measured pre-ejection period, the non-invasively measured ejection period, the determined telediastolic aorta blood pressure, and the determined telesystolic aorta blood pressure, a cardiac mechanical efficiency of the subject as the ratio of left-ventricle telesystolic elastance to aorta effective elastance, according the predetermined relationship. Thus, the present heart-function monitor apparatus can non-invasively and easily monitor the cardiac mechanical efficiency corresponding to the cardiac function of the subject.

(2) According to a second feature of the present invention that includes the first feature (1), the predetermined relationship is defined by a following expression:

$$E_{es}/E_a = (P_{ad}/P_{es})\{1+k(ET/PEP)\}-1$$

where $E_{es}/E_a$ is the cardiac mechanical efficiency, $P_{ad}$ is the telediastolic aorta blood pressure, $P_{es}$ is the telesystolic aorta blood pressure, ET is the ejection period, PEP is the pre-ejection period, and k is a coefficient.

The above expression is obtained based on the fact that when a portion of the time-elastance curve, shown in FIG. 8, between its start end and the maximum elastance $E_{max}$, i.e., the telesystolic elastance $E_{es}$ is approximated by the two straight lines $L_1$, $L_2$, shown in FIG. 9, the cardiac mechanical efficiency $E_{es}/E_a$ can be expressed by using the telediastolic aorta (blood) pressure $P_{ad}$, the telesystolic aorta pressure $P_{es}$, the ejection period ET, the pre-ejection period PEP, and the ratio k of the slope $k_2$ of the line $L_2$ to the slope $k_1$ of the line $L_1$.

(3) According to a third feature of the present invention that includes the second feature (2), the coefficient k of the expression is a variable expressed as a function of at least one of the cardiac mechanical efficiency and a ratio of the ejection period to the pre-ejection period. According to this feature, the cardiac-mechanical-efficiency determining means determines a more reliable cardiac mechanical efficiency. The reason why the coefficient (i.e., above-indicated ratio) k of the expression is a function of at least one of the cardiac mechanical efficiency and the ratio of the ejection period to the pre-ejection period, is that when the cardiac mechanical efficiency and the ratio k are measured by an invasive method, it was found that there is a certain correlation between the ratio k and each of the cardiac mechanical efficiency and the ratio of the ejection period to the pre-ejection period.

(4) According to a fourth feature of the present invention that includes the second feature (2), the coefficient k of the expression is a variable expressed as a function of the cardiac mechanical efficiency and a ratio of the ejection period to the pre-ejection period. According to this feature, the cardiac-mechanical-efficiency determining means determines a still more reliable cardiac mechanical efficiency.

(5) According to a fifth feature of the present invention that includes the fourth feature (4), the coefficient k of the expression is defined by a following expression:

$$k = a \times (E_{es}/E_a)^b + c \times (ET/PEP) + d$$

where a, b, c, and d are constants which are experimentally obtained.

The above expression is obtained based on the fact that the variable k is an exponential function of the cardiac mechanical efficiency measured by the invasive method and the fact that the variable k is a linear function of the ratio, ET/PEP, of the ejection period ET to the pre-ejection period PEP.

(6) According to a sixth feature of the present invention that includes any one of the first to fifth features (1) to (5), the pre-ejection period measuring device comprises an electrocardiograph which includes a plurality of electrodes adapted to contact a body surface of the subject, and which detects, from the subject, an electrocardiogram waveform including a Q wave; a heart-sound detecting device which is located in a body cavity of the subject, at a position in a vicinity of the heart of the subject, and which detects, from the subject, a first heart sound I and a second heart sound II; and means for determining, as the pre-ejection period, a first time period from a time when the Q wave of the electrocardiogram waveform is detected to a time when an end of the first heart sound I is detected. Thus, the pre-ejection period measuring device can non-invasively measure the pre-ejection period PEP with accuracy.

(7) According to a seventh feature of the present invention that includes the sixth features (6), the ejection-period measuring device comprises means for determining a second time period from the time when the Q wave of the electrocardiogram waveform is detected to a time when a start of the second heart sound II is detected, and determining, as the ejection period, a third time period obtained by subtracting the first time period from the second time period. Thus, the ejection-period measuring device can non-invasively measure the ejection period ET with accuracy.

(8) According to an eighth feature of the present invention that includes any one of the first to sixth features (1) to (6), the ejection-period measuring device comprises a heart-sound detecting device which is worn on the subject, at a position in a vicinity of the heart of the subject, and which detects, from the subject, a first heart sound I and a second heart sound II; and means for determining, as the ejection period, a time period from a time when an end of the first heart sound I is detected to a time when a start of the second heart sound II is detected. The ejection-period measuring device can non-invasively measure the ejection period ET with accuracy.

(9) According to a ninth feature of the present invention that includes any one of the first to sixth features (1) to (6), the ejection-period measuring device comprises means for determining, as the ejection period, a time period from a time of occurrence of a minimum point of a waveform representing the aorta blood pressure estimated by the aorta-blood-pressure estimating means to a time of occurrence of a notch of the waveform, the notch occurring at a time when an aortic valve of the heart is closed. The ejection-period measuring device can non-invasively measure the ejection period ET with accuracy.

(10) According to a tenth feature of the present invention that includes any one of the first to ninth features (1) to (9), the telediastolic-aorta-pressure determining means comprises an electrocardiograph which includes a plurality of electrodes adapted to contact a body surface of the subject, and which detects, from the subject, an electrocardiogram waveform including a Q wave; and means for determining, as the telediastolic aorta blood pressure, a blood pressure which is estimated by the aorta-pressure estimating means as an aorta blood pressure at a time when the Q wave of the electrocardiogram waveform is detected by the electrocardiograph. The telediastolic-aorta-pressure determining means can non-invasively determine the telediastolic aorta blood pressure with accuracy.

(11) According to an eleventh feature of the present invention that includes any one of the first to tenth features (1) to (10), the telesystolic-aorta-pressure determining means comprises means for determining, as the telesystolic aorta blood pressure, a blood pressure which is estimated by the aorta-pressure estimating means as an aorta mean blood pressure. The telesystolic-aorta-pressure determining means can non-invasively determine the telesystolic aorta blood pressure with accuracy.

(12) According to a twelfth feature of the present invention that includes any one of the first to tenth features (1) to (10), the telesystolic-aorta-pressure determining means comprises an electrocardiograph which includes a plurality of electrodes adapted to contact a body surface of the subject, and which detects, from the subject, an electrocardiogram waveform including a T wave; and means for determining, as the telesystolic aorta blood pressure, a blood pressure which is estimated by the aorta-pressure estimating means as an aorta blood pressure at a time when an end of the T wave of the electrocardiogram waveform is detected by the electrocardiograph. The telesystolic-aorta-pressure determining means can non-invasively determine the telesystolic aorta blood pressure with accuracy.

(13) According to a thirteenth feature of the present invention that includes any one of the first to tenth features (1) to (10), the telesystolic-aorta-pressure determining means comprises a heart-sound detecting device which is worn on the subject, at a position in a vicinity of the heart of the subject, and which detects at least a second heart sound II from the subject; and means for determining, as the telesystolic aorta blood pressure, a blood pressure which is estimated by the aorta-pressure estimating means as an aorta blood pressure at a time when a start of the second heart sound II is detected by the heart-sound detecting device. The telesystolic-aorta-pressure determining means can non-invasively determine the telesystolic aorta blood pressure with accuracy.

(14) According to a fourteenth feature of the present invention that includes any one of the first to thirteenth features (1) to (13), the pre-ejection period measuring device non-invasively measures, each time the heart contracts and expands, a pre-ejection period from a time when the contraction of the cardiac muscle of the left ventricle of the heart starts, to a time when the ejection of the blood from the left ventricle starts; the ejection period measuring device non-invasively measures, each time the heart contracts and expands, an ejection period during which the blood is ejected from the left ventricle starts; the aorta-pressure estimating means estimates, each time the heart contracts and expands, blood pressure values in the aorta of the subject; each time the heart contracts and expands, the telediastolic-aorta-pressure determining means determines, based on the estimated blood pressure values of the aorta, a telediastolic blood pressure in the aorta at a telediastolic time of the heart; each time the heart contracts and expands, the telesystolic-aorta-pressure determining means determines, based on the estimated blood pressure values of the aorta, a telesystolic blood pressure in the aorta at a telesystolic time of the heart; and, each time the heart contracts and expands, the cardiac-mechanical-efficiency determining means determines, based on the measured pre-ejection period, the measured ejection period, the determined telediastolic aorta blood pressure, and the determined telesystolic aorta blood pressure, a cardiac mechanical efficiency value of the subject according to the predetermined relationship between (A) cardiac mechanical efficiency and (B) (b1) pre-ejection period, (b2) ejection period, (b3) telediastolic aorta blood pressure and (b4) telesystolic aorta blood pressure, and wherein the apparatus further comprises a display device which displays, along an axis indicative of time, the cardiac mechanical efficiency values which are successively determined by the cardiac-mechanical-efficiency determining means as the heart successively contracts and expands. Since the display device displays a timewise trend of the successively determined cardiac mechanical efficiency values, a doctor or a nurse, for example, can recognize, when the cardiac function of a patient who is undergoing a surgical operation is lowering, the tendency or direction of change of the cardiac function, from the displayed timewise trend. Therefore, the doctor or nurse can estimate an abnormality of the cardiac function before the cardiac function actually indicates the abnormality.

(15) According to a fifteenth feature of the present invention that includes any one of the first to fourteenth features (1) to (14), the aorta-pressure estimating means comprises a blood-pressure measuring device which includes an inflatable cuff adapted to be wound around a body portion of the subject, and which measures at least one blood pressure of the subject when an air pressure in the cuff is changed; a pulse-wave sensor which is adapted to be pressed against an artery of the subject via a skin tissue of the subject so as to flatten a portion of a wall of the artery, and which detects a pressure pulse wave transmitted thereto from the artery via the flattened wall portion of the artery and the skin tissue; relationship determining means for determining a relationship between blood pressure and pressure-pulse-wave magnitude, based on at least one blood pressure measured by the blood-pressure measuring device and at least one magnitude of the pressure pulse wave detected by the pulse-wave sensor; and means for calibrating, according to the determined relationship, instantaneous magnitudes of the pressure pulse wave detected by the pulse-wave sensor, and thereby providing a waveform representing the estimated aorta blood pressure values of the subject.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which.

DETAILED DESCRIPTION OF THE PREFERRED EMBODIMENTS

Figure 1:
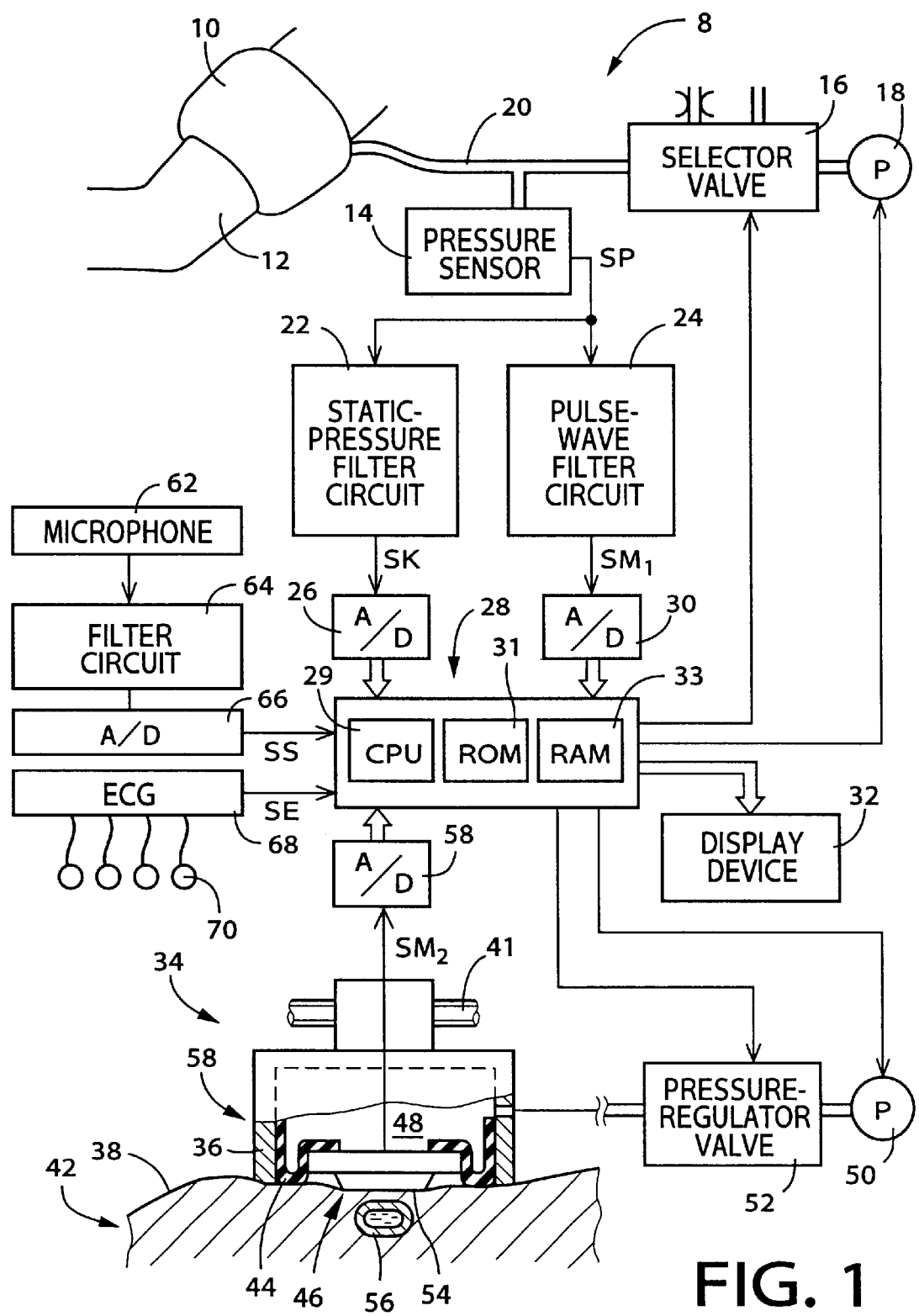
FIG. 1 is a diagrammatic view for explaining the construction of a heart-function monitor apparatus to which the present invention is applied.

Referring first to FIG. 1, there is shown a heart-function monitor apparatus 8 embodying the present invention.

In FIG. 1, reference numeral 10 designates an inflatable cuff which is provided by a belt-like cloth bag and a rubber bag accommodated in the cloth bag. The cuff 10 is worn on a patient by being wound around, for example, an upper arm 12 of the patient. A pressure sensor 14, a selector valve 16, and an air pump 18 are connected to the cuff 10 via a piping 20.

The selector valve 16 is selectively placed in an INFLATION position, a SLOW-DEFLATION position, and a QUICK-DEFLATION position. In the INFLATION position, the selector valve 16 permits pressurized air to be supplied from the air pump 18 to the cuff 10; in the SLOW-DEFLATION position, the valve 16 permits the pressurized air to be slowly discharged from the cuff 10 into the atmosphere; and in the QUICK-DEFLATION position, the valve 16 permits the pressurized air to be quickly discharged from the cuff 10 into the atmosphere.

The pressure sensor 14 detects an air pressure in the cuff 10, and supplies a pressure signal, SP, representing the detected pressure, to a static-pressure filter circuit 22 and a pulse-wave filter circuit 24. The static-pressure filter circuit 22 includes a low-pass filter and transmits, as a cuff-pressure signal SK, a static ("DC") component of the signal SP. The cuff pressure signal SK represents a static pressure, P, of the cuff 10 (hereinafter, referred to simply as the "cuff pressure P"). The cuff-pressure signal SK is supplied to a control device 28 via an analog-to-digital (A/D) converter 26. The pulse-wave filter circuit 24 includes a band-pass filter and transmits, as a pulse-wave signal $SM_1$, an oscillating ("AC") component of the signal SP. The pulse-wave signal $SM_1$ is supplied to the control device 28 via an A/D converter 30.

The pulse-wave signal $SM_1$ represents a pulse wave, i.e., an oscillatory pressure wave which is produced from a brachial artery (not shown) of the patient in synchronism with the heartbeat of the patient and is transmitted to the cuff 10 via a skin tissue positioned between the artery and the cuff 10. Thus, the pulse-wave filter circuit 24 serves as a pulse-wave sensor which detects a pulse wave from a body portion of a living subject.

The control device 28 is provided by a microcomputer which includes a central processing unit (CPU) 29, a read only memory (ROM) 31, a random access memory (RAM) 33, and an input and output (I/O) port (not shown). The CPU 29 processes input signals according to control programs pre-stored in the ROM 31 by utilizing a temporary-storage function of the RAM 33, and outputs drive signals to the selector valve 16 and the air pump 18 via the I/O port and respective drive circuits (not shown) so as to regulate the cuff pressure P. In addition, the CPU 29 of the control device 28 operates for determining, according to well-known oscillometric method, blood pressure ("BP") values (e.g., systolic and diastolic BP values; referred to as the "proper BP values" if appropriate) of the patient, based on the variation of respective amplitudes of heartbeat-synchronous pulses of the pulse wave represented by the pulse-wave signal $SM_1$ obtained while the cuff pressure P is decreased slowly at a rate of about 3 mmHg/sec after the cuff pressure P is quickly increased up to a predetermined target pressure. The control device 28 commands a display device 32 including a cathode ray tube (CRT), to indicate the thus determined BP values on the CRT. The control device 28 repeats this BP measurement using the cuff 10, at predetermined intervals of time.

As shown in FIG. 1, the present monitor apparatus further includes a pulse-wave detector probe 34. The detector probe 34 includes an outer case (not shown) which accommodates a container-like sensor housing 36 and which is detachably attached to a body surface 38 of a wrist 42 of the patient with a pair of bands (not shown) which are fastened around the wrist 42. The wrist 42 is opposite to the upper arm 12 around which the cuff 10 is wound. The outer case support a feed screw 41 which is threadedly engaged with a projection of the sensor housing 36 and which is driven or rotated by an electric motor (not shown) to move the housing 36 in opposite directions intersecting a radial artery 56. With the outer case being attached to the body surface 38 with the help of the bands, an open end of the housing 36 contacts the body surface 38 of the wrist 42.

A pulse-wave sensor 46 is supported by the sensor housing 36 via an elastic diaphragm 44, such that the pulse-wave sensor 46 is displaceable relative to the housing 36, when the diaphragm 44 is inflated, so as to be advanceable out of the open end of the housing 36. The housing 36, the diaphragm 44 and the pulse wave sensor 46 cooperate with one other to define a pressure chamber 48, to which pressurized air is supplied from an air pump 50 via a pressure-regulator valve 52. Thus, the pulse-wave sensor 46 is pressed against the body surface 38 with a pressing force corresponding to the air pressure in the pressure chamber 48. As far as the present embodiment is concerned, the pressing force applied to the pulse-wave sensor 46 is expressed in terms of the air pressure (unit: mmHg) in the pressure chamber 48.

The sensor housing 36 and the elastic diaphragm 44 cooperate with each other to provide a pressing device 58 which presses the pulse-wave sensor 46 against the radial artery 56 via the skin tissue; and the feed screw 41 and the electric motor (not shown) cooperate with each other to provide a pressing-position changing device or a sensor moving device which moves the pulse-wave sensor 46 in the direction intersecting the radial artery 56 and thereby changes the pressing position where the sensor 46 presses the artery 56.

The pulse-wave sensor 46 includes a plurality of semi-conductor pressure-sensing elements (not shown) which are provided in a plane surface of a semiconductor substrate, such as a monocrystalline silicon. The plane surface provides a press surface 54 of the pulse-wave sensor 46. The pressure-sensing elements are arranged, in the press surface 54, at small intervals of distance (e.g., 0.2 mm) in a direction parallel to the feed screw 41, that is, the direction in which the sensor 46 is moved by the screw 41. The pulse-wave sensor 46 is pressed on the body surface 38 of the wrist 42 such that the array of pressure-sensing elements cross over, or intersect, the radial artery 56. Thus, each of the pressure-sensing elements of the pulse-wave sensor 46 detects a pressure pulse wave, i.e., an oscillatory pressure wave which is produced from the radial artery 56 in synchronism with the heartbeat of the patient and is transmitted to the body surface 38 or the press surface 54, and produces a pulse-wave signal, $SM_2$, representing the detected pulse wave. The respective pulse-wave signals $SM_2$ produced by the pressure-sensing elements of the pulse-wave sensor 46 are supplied to the control device 28 via an A/D converter 58.

The control device 28 operates, according to the control programs pre-stored in the ROM 31, for supplying drive signals to the air pump 50 and the pressure-regulator valve 52 via respective drive circuits (not shown), so as to regulate the air pressure in the pressure chamber 48. When the control device 28 operates for carrying out, for example, a BP-monitor operation, the control device 28 collects, while slowly changing (e.g., increasing) the pressure in the chamber 48, the pulse-wave signals $SM_2$ supplied from the individual pressure-sensing elements of the pulse-wave sensor 46. Based on the thus collected pulse-wave signals $SM_2$, the control device 28 determines an optimum air pressure (i.e., optimum pressing force), $P_{HDPO}$, to be applied to the pulse-wave sensor 46, by identifying an air pressure value in the chamber 48 at the time when a portion of the wall of the radial artery 56 is partly flattened under the pressing force of the pulse-wave sensor 46. Since the manner of determination of the optimum pressing force is well known in the art, no more description is provided.

Based on the collected pulse-wave signals $SM_2$, the control device 28 additionally selects an optimum pressure-sensing element located right above the center of the radial artery 56, by identifying one of the pressure-sensing elements of the pulse wave sensor 46 that provides a pulse wave signal $SM_2$ having the greatest amplitude of the respective amplitudes provided by all the pressure-sensing elements. Thus, the control device 28 controls the pressure regulator valve 52 so as to maintain the pressure of the chamber 48 at the determined optimum air pressure $P_{HDPO}$, and receives the pulse-wave signal $SM_2$ from the selected optimum pressure-sensing element with the chamber 48 being maintained at the optimum air pressure $P_{HDPO}$. It is speculated that, since the optimum pressure-sensing element is located right above the center of the artery 56, the pulse-wave signal $SM_2$ supplied from the optimum element is free of the influence due to the elastic or tensile force produced in the wall of the artery 56 and accordingly accurately represents BP in the artery 56. That is, the waveform of the pulse-wave signal $SM_2$ supplied from the optimum pressure-sensing element accurately indicates the instantaneous variation of BP of the patient.

Figure 2:
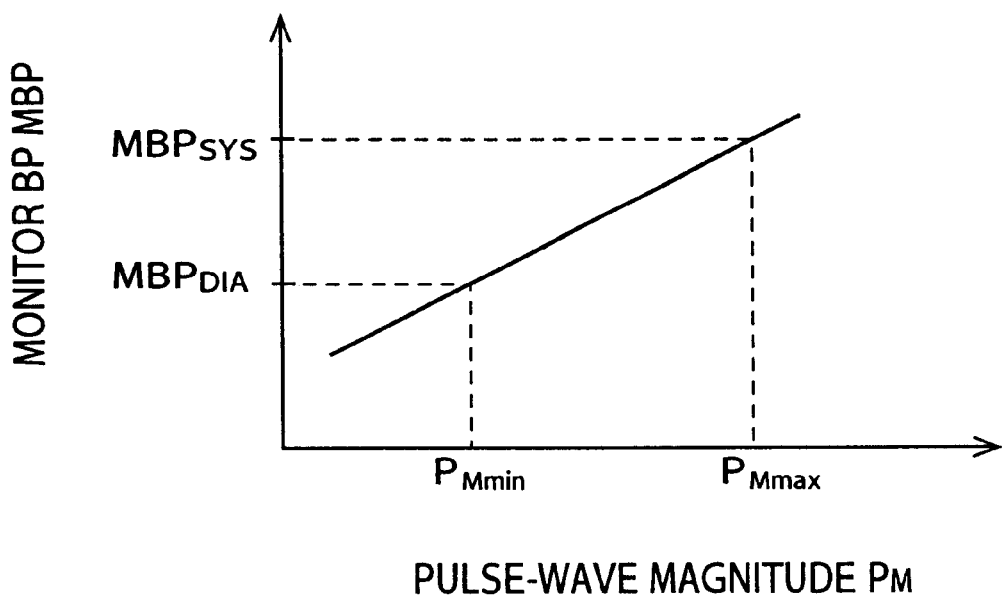
FIG. 2 is a graph representing a relationship between blood pressure ("BP") and pulse-wave magnitude, which is used by the apparatus of FIG. 1 to estimate an arterial-BP waveform based on a pressure pulse wave detected by a pressure-pulse-wave sensor of the apparatus.

In addition, each time a systolic and a diastolic BP values, $BP_{SYS}$, $BP_{DIA}$, are measured using the cuff 10, the control device 28 operates, according to the control programs pre-stored in the ROM 31, for determining a relationship between blood pressure and pulse wave magnitude (referred to as the "MBP-$P_M$ relationship"), as shown in FIG. 2, based on the measured systolic and diastolic BP values $BP_{SYS}$, $BP_{DIA}$ and a maximum and a minimum magnitude (i.e., upper-peak and lower-peak magnitudes), $P_{Mmax}$, $P_{Mmin}$, of one heartbeat-synchronous pulse of the pulse-wave signal $SM_2$ supplied from the pulse-wave sensor 46 (i.e., the optimum pressure-sensing element thereof). The difference between the maximum and minimum magnitudes $P_{Mmax}$, $P_{Mmin}$ of each heartbeat-synchronous pulse is defined as the amplitude of the each pulse. According to the thus determined MBP-$P_M$ relationship, the control device 28 successively or continuously determines a systolic and a diastolic BP value, $MBP_{SYS}$, $MBP_{DIA}$, (i.e., estimated or monitor BP values) of the patient, based on a maximum and a minimum magnitude $P_{Mmax}$, $P_{Mmin}$ of each of respective heartbeat-synchronous pulses of the pulse-wave signal $SM_2$ detected after the MBP-$P_M$ relationship is determined, and commands the display device 32 to display continuously the monitor BP values $MBP_{SYS}$, $MBP_{DIA}$, in digits, that are determined for the each of the successive heartbeat-synchronous pulses. In addition, the control device 28 commands the display device 32 to display continuously a waveform of the pulse-wave signal $SM_2$ supplied from the optimum pressure-sensing element. This waveform indicates the monitor BP values MBP thus determined for the each successive pulse.

The MBP-$P_M$ relationship shown in FIG. 2 is defined by the following expression (1):

$$MBP = A \cdot P_M + B \tag{1}$$

where

A is a constant representing a slope, and

B is a constant representing an intercept.

Figure 5:
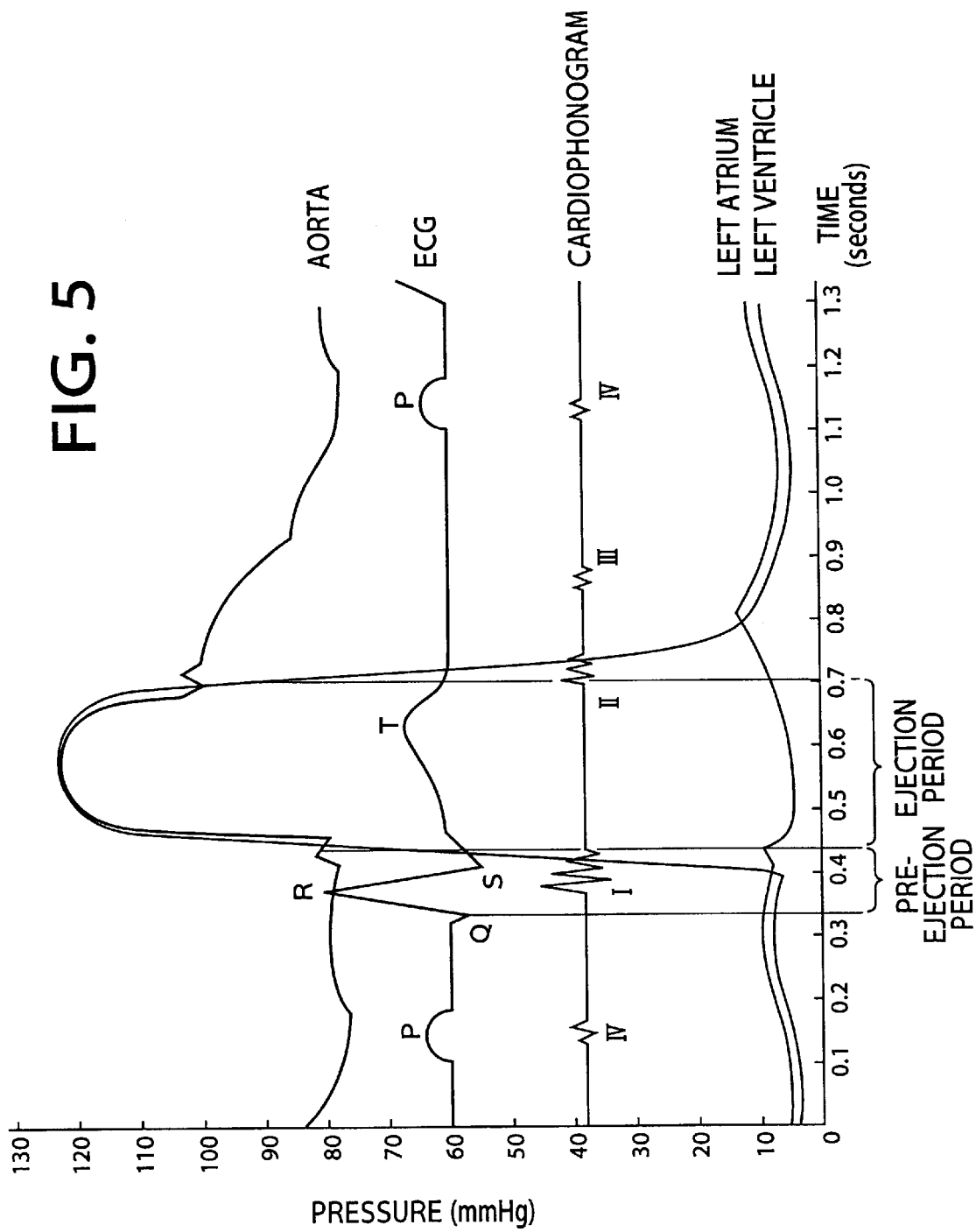
FIG. 5 is a time chart representing a relationship between a pre-ejection period and an ejection period respectively determined by a pre-ejection-period determining means and an ejection-period determining means of the apparatus of FIG. 1, and an aortic-BP waveform, an ECG waveform, and a cardiophonogram obtained by the apparatus.

In FIG. 1, a heart-sound microphone 62 which functions as a heart-sound sensor is provided in the vicinity of the heart of the patient so as to detect heart sounds produced from the heart, and produces a heart-sound signal, SS, representing the detected heart sounds. The microphone 62 may be worn on a body surface of the patient, but it is preferred that the microphone 62 be provided in a body cavity of the patient, such as the esophagus. The heart-sound signal SS produced by the microphone 62 is supplied to the control device 28 via an amplifier (not shown), a band-pass filter 64 for removing noise from the signal SS, and an A/D converter 66. The heart sounds represented by the heart-sound signal SS include, as shown in FIG. 5, a first sound I corresponding to the closing of the mitral valve and the opening of the aortic valve, and a second sound II corresponding to the closing of the aortic valve.

An electrocardiograph ("ECG") 68 includes a plurality of electrodes 70 which are adhered to a body surface of the patient such that the adhered electrodes 70 surround the heart of the patient, detects, through the adhered electrodes 70, an electrocardiogram ("ECG") waveform induced by the heart, and produces an ECG signal, SE, representing the detected ECG waveform. The ECG signal SE is supplied to the control device 28. Each period or cycle of the ECG signal SE includes, as shown in FIG. 5, well-known P wave, Q wave, R wave, S wave and T wave in this order.

The control device 28 processes the ECG signal SE, the heart-sound signal SS and the pulse-wave signal $SM_2$ so as to determine a telediastolic aortic BP value, $P_{ad}$, a telesystolic aortic BP value, $P_{es}$, a pre-ejection period, PEP, and an ejection time or period, ET, and determines, based on the thus determined values $P_{ad}$, $P_{es}$, PEP, ET, a cardiac mechanical efficiency, $E_{es}/E_a$, according to a predetermined expression (2):

$$E_{es}/E_a = (P_{ad}/P_{es})\{1+k(ET/PEP)\}-1 \qquad (2)$$

The cardiac mechanical efficiency $E_{es}/E_a$ is determined for each of successive heartbeat-synchronous pulses of the pulse-wave signal $SM_2$, and is stored in a memory device (not shown) such as a hard disk, a semiconductor memory card, or a magnetic tape. The control device 28 controls the display device 32 or a printer (not shown) to display or print a timewise trend of the thus determined cardiac mechanical efficiency values $E_{es}/E_a$.

Figure 3:
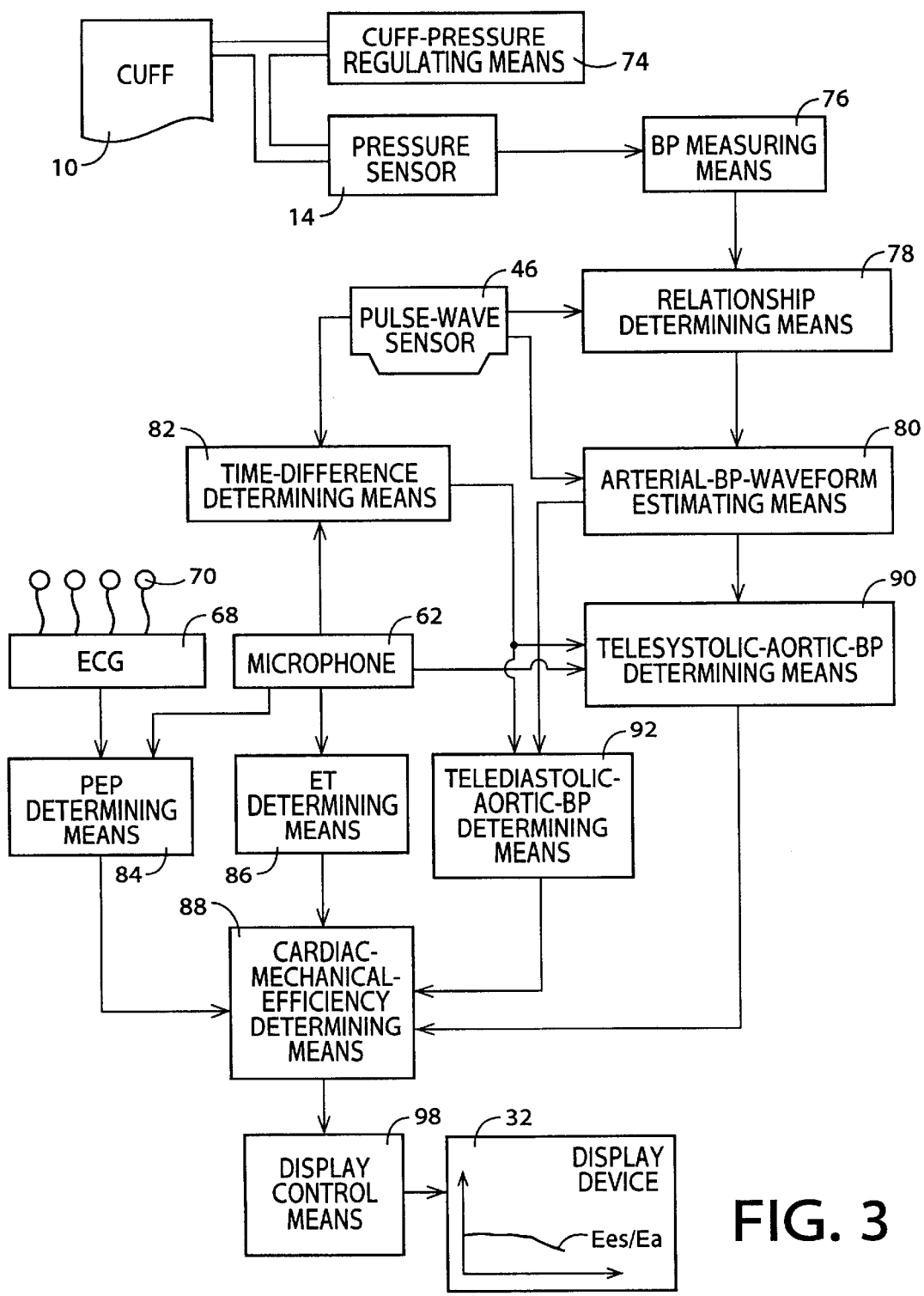
FIG. 3 is a diagrammatic view for explaining important control functions of a control device of the apparatus of FIG. 1.

FIG. 3 shows important control functions of the control device 28. In a BP measuring operation, the pressure sensor 14 detects the pressing pressure of the inflatable cuff 10 that is changed by a cuff-pressure regulating means 74. A BP measuring means 76 measures, according to the oscillometric method or the Korotkoff-sound method, a systolic BP value $BP_{SYS}$, a mean BP value $BP_{MEAN}$, and a diastolic BP value $BP_{DIA}$ (i.e., proper BP values) of the patient, based on the change of the pulse-wave signal $SM_1$ (e.g, the change of respective amplitudes of heartbeat-synchronous pulses of the signal $SM_1$), or the change of Korotkoff sounds (e.g., the first and last detection of the sounds) that are obtained while the pressing pressure of the cuff 10 is changed slowly at the rate of about 2 to 3 mmHg/sec by the cuff-pressure regulating means 74.

A relationship determining means 78 determines, in advance, a MBP-$P_M$ relationship, shown in FIG. 2, between blood pressure BP and pulse-wave magnitude $P_M$, based on the pulse-wave signal $SM_2$ detected by the above-indicated optimum pressure-sensing element (hereinafter, referred to as the "active element") of the pulse-wave sensor 46 and the BP values measured by the BP measuring means 76.

Figure 4:
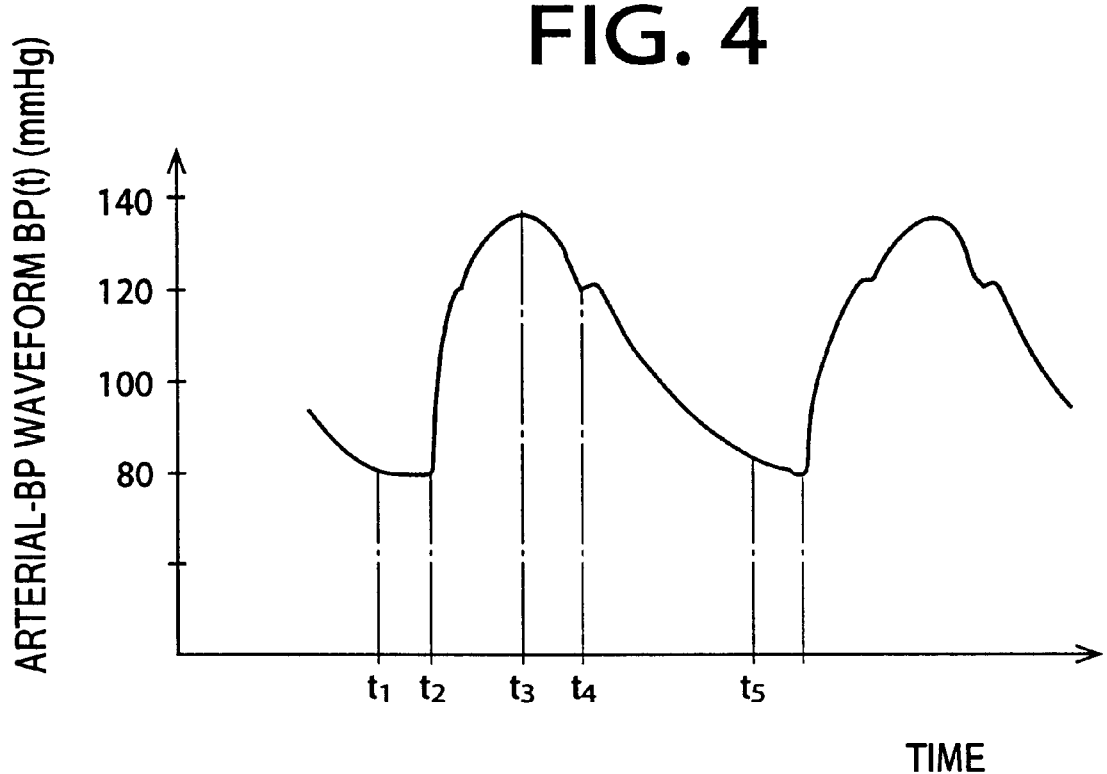
FIG. 4 is a graph representing an arterial-BP waveform estimated by an arterial-BP-waveform estimating means of the apparatus of FIG. 1.

An estimated-BP determining means (or an arterial-BP-waveform estimating means) 80 continuously determines, according to the MBP-$P_M$ relationship shown in FIG. 2, estimated or monitor BP values of the patient based on at least one magnitude of each of successive heartbeat-synchronous pulses of the pulse-wave signal $SM_2$ detected by the above-indicated active element of the pulse-wave sensor 46, and outputs an arterial-BP waveform, BP(t), as shown in FIG. 4, which represents the estimated or monitor BP values of the patient. This arterial-BP waveform BP(t) indicates the waveform of BP of the brachial artery of the patient, but corresponds to that of the aorta of the patient. Therefore, the arterial-BP-waveform estimating means 80 functions as an estimated-aortic-BP determining means, and the arterial-BP waveform BP(t) represents estimated aortic BP values. In the case, however, where an aortic-BP waveform cannot be estimated by the brachial-artery-BP waveform BP(t) for some reasons, a predetermined transfer function may be employed to determine an aortic-BP waveform based on the brachial-artery-BP waveform BP(t).

A time-difference determining means 82 determines a time difference, TD, between the end of the first sound I detected by the heart-sound microphone 62 and the rising point (i.e., minimum or lower-peak point) of a corresponding heartbeat-synchronous pulse of the pulse-wave signal $SM_2$ detected by the pulse-wave sensor 46. Since the end of the first sound I indicates the time when the left ventricle of the heart starts ejecting blood into the aorta, the time difference TD is equal to a time needed for the aortic BP to propagate from the aorta to the radial artery 56 against which the sensor 46 is pressed. In the case where it is difficult to specify the end of the first heart sound I, the first sound I may be replaced by the Q wave, R wave, or S wave of the ECG waveform each of which indicates the time when the heart-ventricle muscle starts excitation, that is, the left ventricle starts contraction.

A PEP determining means 84 non-invasively determines a pre-ejection period PEP between the start of contraction of the cardiac muscle of the left ventricle and the start of ejection of blood from the left ventricle. For example, the PEP determining means 84 determines, for each of successive heartbeat-synchronous pulses of the heart, the pre-ejection period PEP (seconds) by counting reference clock pulses from the time when the Q wave of the ECG waveform is detected to the time when the end of the first sound I is detected. Alternatively, the PEP determining means 84 may determine the pre-ejection period PEP by subtracting the time difference TD determined by the means 82, from a time between the time when the Q wave of the ECG waveform is detected and the time when the rising point of the aortic-BP waveform is detected. In the case where the time difference between the Q wave and the R wave of the ECG waveform can be neglected, the Q wave may be replaced with the R wave that is more easily detected. Since the pre-ejection period PEP is, as shown in the time chart of FIG. 5, the time between the time when the cardiac muscle of the left ventricle of the heart starts contraction and the time when the left ventricle starts outputting blood, i.e., the aortic valve opens, the period PET is called as an isovolumetric contraction period or time.

An ET determining means 86 non-invasively determines an ejection period ET during which the left ventricle of the heart outputs blood. For example, the PT determining means 86 determines, for each of successive heartbeat-synchronous pulses of the heart, the ejection period ET (seconds) by counting reference clock pulses from the time when the end of the first heart sound I is detected to the time when the start of the second heart sound II is detected. Alternatively, the ET determining means 86 may determine the ejection period ET by first measuring a time period from the Q wave of the ECG waveform is detected to the time when the start of the second sound II is detected, so as to determine the sum, (PEP+ET), of the pre-ejection period PEP and the ejection period ET, that is, a time period during which the heart contracts, and then subtracting, from the sum (PEP+ET), the pre-ejection period PEP determined by the means 84. In this case, too, the R wave may be used in place of the Q wave. Otherwise, the ET determining means 86 may determine the ejection period ET by measuring a time period from the time ($t_2$ in FIG. 4) when the rising point of each heartbeat-synchronous pulse of the estimated arterial-BP waveform BP(t) to the time ($t_4$) when the notch of the each pulse that corresponds to the time when the aortic valve is closed.

A telesystolic-aortic-BP determining means 90 determines a telesystolic-aortic-BP ("TSA-BP") value, $P_{es}$, that is, a BP value in the aorta at the end of the contraction of the left ventricle, based on the estimated arterial-BP waveform BP(t) provided by the means 80, the time difference TD determined by the means 82, and the heart-sound signal SS detected by the microphone 62. For example, since the start of the second heart sound II is detected when the aortic valve is closed, that is, when the contraction of the left ventricle ends, and the aortic BP at the start of the second sound II propagates to the radial artery 56 after the time difference TD, the start of the second sound II is identified, and a BP value corresponding to a magnitude taken or indicated by the estimated arterial-BP waveform BP(t) at a time after the time difference TD from the time when the start of the second sound II is identified, is determined as the TSA-BP value $P_{es}$.

A telediastolic-aortic-BP determining means 92 determines a telediastolic-aortic-BP ("TDA-BP") value, $P_{ad}$, that is, a BP value in the aorta at the end of the expansion of the left ventricle, based on the estimated arterial-BP waveform BP(t) provided by the means 80. For example, a BP value corresponding to a magnitude taken or indicated by the estimated arterial-BP waveform BP(t) at a time after the time difference TD from the time when the Q wave of the ECG waveform that corresponds to the start of contraction of the cardiac muscle, that is, the end of expansion of the same is detected, is determined as the TDA-BP value $P_{ad}$.

A cardiac-mechanical-efficiency determining means 88 determines, according to a predetermined relationship, e.g., the relationship defined by the above-indicated expression (2), a cardiac mechanical efficiency $E_{es}/E_a$, i.e., the ratio of a left-ventricle telesystolic elastance $E_{es}$ to an aortic effective elastance $E_a$, based on the pre-ejection period PEP determined by the means 84, the ejection period ET determined by the means 86, the TSA-BP value $P_{es}$ determined by the means 90, and the TDA-BP value $P_{ad}$ determined by the means 92. In the case where the relationship defined by the expression (2) is employed, "k" occurring to the expression (2) may be a mathematical function of the cardiac mechanical efficiency $E_{es}/E_a$, or a function of the ratio, ET/PEP, of the ejection period ET to the pre-ejection period PEP, or a function of the cardiac mechanical efficiency $E_{es}/E_a$ and the ratio ET/PEP. In each case, the function is experimentally determined in advance. Alternatively, "k" may be a constant (e.g., 0.7) which is experimentally determined in advance. For example, in the case where "k" is a function of the cardiac mechanical efficiency $E_{es}/E_a$ and the ratio ET/PEP, the function "k" may be defined by the following expression (3):

$$k = a \times (E_{es}/E_a)^b + c \times (ET/PEP) + d \qquad (3)$$

where a, b, c, and d are constants.

The above constants a, b, c, d are determined as follows, according to a non-linear least square method, by using a cardiac mechanical efficiency $E_{es}/E_a$ which is measured by an invasive method, the ratio ET/PEP, and the function k which is determined based on the measured value $E_{es}/E_a$ and the ratio ET/PEP according to the expression (2):

$$k = 0.72 \times (E_{es}/E_a)^{0.41} + 0.045 \times (ET/PEP) - 0.091$$

Here, the expression (2) is described in detail and the ratio ET/PEP. A relationship between an inner volume, V, of the left ventricle of the heart and an inner pressure, P, of the same may be expressed by a two-dimensional coordinate system, shown in FIG. 6, which has a pressure axis and a volume axis. A pressure-volume loop representing each beat cycle of the heart has a generally rectangular shape including an isovolumetric expansion line, $L_3$, an equal-pressure expansion line, $L_4$, an isovolumetric contraction line, $L_5$, and an equal-pressure contraction line, $L_6$. In the coordinate system, a symbol, $V_0$, indicates a left-ventricle unstressed volume that is an inner volume of the left ventricle at the time when the inner pressure of the same is zero. The left-ventricle unstressed volume $V_0$ is, as shown in FIG. 7, the intersection point of the volume axis and a telesystolic pressure-volume line, $L_{es}$, that is a line representing a relationship between the left-ventricle volume V and the end point of the equal-pressure contraction that is the intersection point of the two lines $L_3$, $L_6$.

Figure 6:
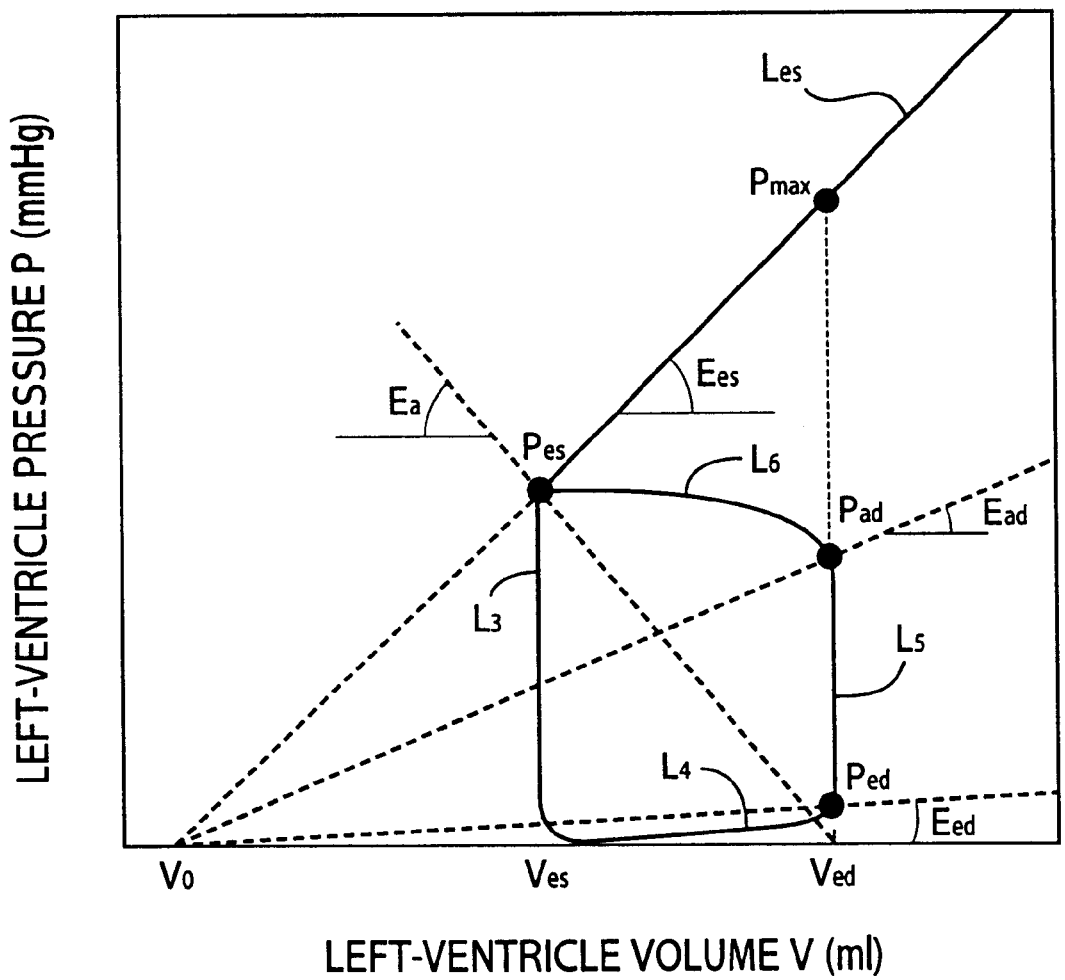
FIG. 6 is a graph showing a one-pulse loop representing a relationship between an inner volume and an inner pressure of the left ventricle of a living subject.
Figure 7:
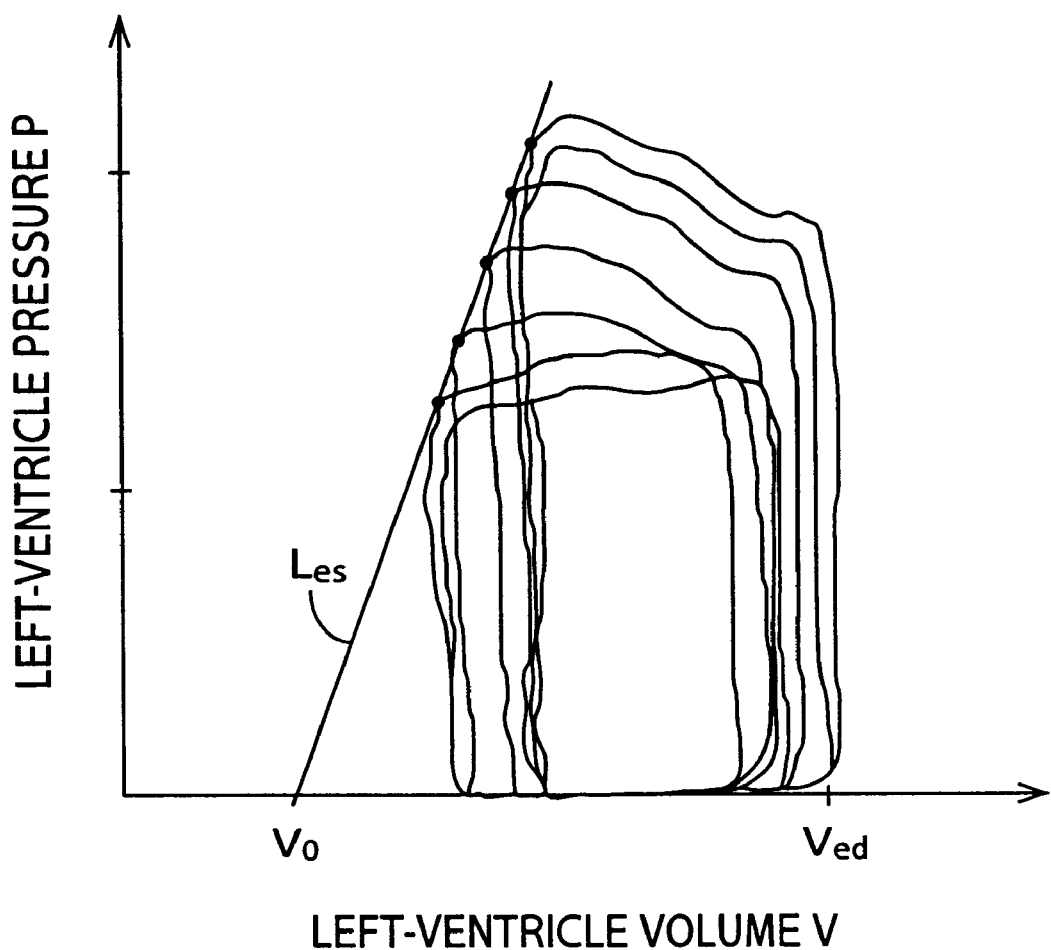
FIG. 7 is a graph for explaining a relationship between various pressure-volume loops and a telesystolic pressure-volume line, $L_{es}$.

On the generally rectangular, pressure-volume loop shown in FIG. 6, an elastance, E(t), is obtained by dividing the continuously obtained inner pressure P(t) of the left ventricle by the difference, (V(t)-$V_0$), of the inner volume, V(t), of the left ventricle and the left-ventricle unstressed volume $V_0$. Thus, the elastance E(t) is also called as a pressure-volume ratio. Therefore, the left-ventricle telesystolic elastance $E_{es}$ is defined as the pressure-volume ratio at the end of contraction of the left ventricle, that is, the slope of the telesystolic pressure-volume line $L_{es}$. The elastance $E_{es}$ indicates a magnitude corresponding to the basic contracting force of the heart, and is used as a cardiac-function index. In addition, the aortic effective elastance $E_a$ is defined as the slope of a line, $L_a$, connecting between the end point of the equal-pressure contraction, and a telediastolic volume, $V_{ed}$, on the volume axis.

Figure 8:
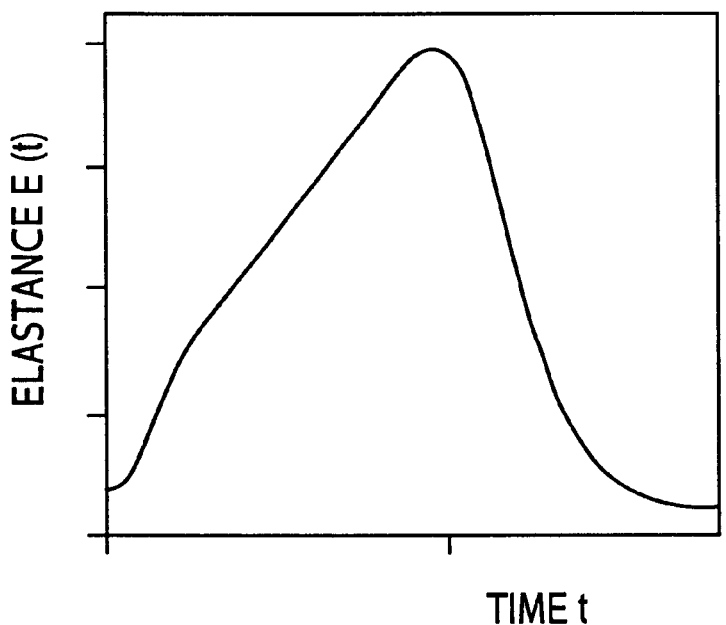
FIG. 8 is a graph showing a curve representing a relationship between elastance (i.e., pressure-volume ratio), E(t), and time, t, that corresponds to the one-pulse pressure-volume loop of FIG. 6.
Figure 9:
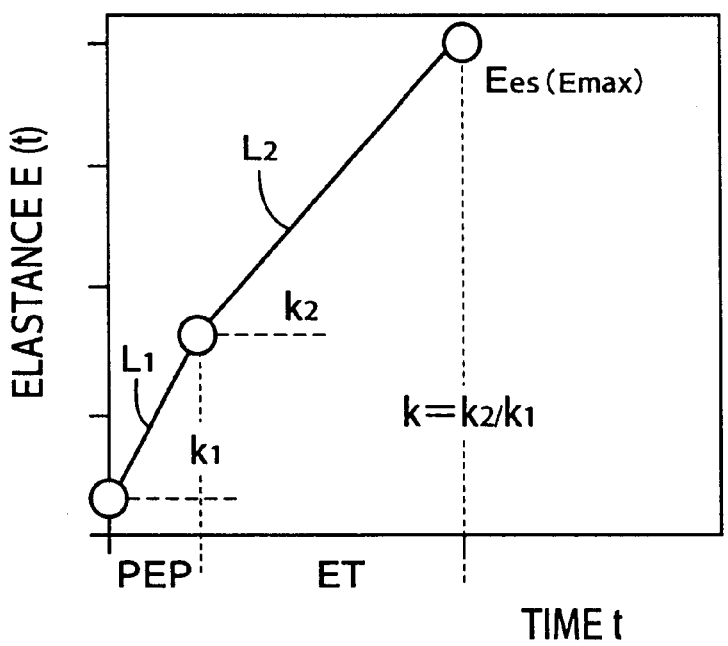
FIG. 9 is a graph showing two straight lines which cooperate with each other to approximate a portion of the curve of FIG. 8 between the start thereof and a maximum elastance (i.e., maximum pressure-volume ratio), $E_{max}$, thereof.

FIG. 8 shows a two-dimensional coordinate system having an axis of ordinate representing the elastance E(t) continuously calculated from the pressure-volume loop shown in FIG. 6, and an axis of abscissa representing time, t. Thus, FIG. 8 shows a length of the elastance E(t) that corresponds to one beat cycle of the heart, i.e., one heartbeat-synchronous pulse. FIG. 9 shows two straight lines, $L_1$, $L_2$ that approximates a first half portion of the pressure-volume-ratio curve between the start point thereof and a maximum pressure-volume ratio, $E_{max}$, i.e., the left-ventricle telesystolic elastance $E_{es}$. The first straight line $L_1$ approximates a portion of the curve that corresponds to the pre-ejection period PEP, and the second straight line $L_2$ approximates another portion of the curve that corresponds to the ejection period ET.

An elastance, $E_{ad}$, at the end of the pre-ejection period PEP is defined as the slope of a straight line, shown in FIG. 6, connecting between the intersection point of the isovolumetric contraction line $L_5$ and the equal-pressure contraction line $L_6$, and the left-ventricle unstressed volume $V_0$, and accordingly is obtained by dividing the inner pressure of the left ventricle at the end of the pre-ejection period PEP by the difference ($V_{ed}$-$V_0$) of the left-ventricle telediastolic volume $V_{ed}$ and the unstressed volume $V_0$. Meanwhile, at the end of the pre-ejection period PEP, the inner pressure of the left ventricle is equal to that of the aorta, which is substantially equal to an aortic pressure, $P_{ad}$, at the start of the pre-ejection period PEP, i.e., the end of expansion of the left ventricle. Thus, the elastance E(t) at the end of the pre-ejection period PEP can be obtained by dividing the telediastolic aortic pressure $P_{ad}$ by the difference ($V_{ed}$-$V_0$) of the telediastolic volume $V_{ed}$ and the unstressed volume $V_0$. Therefore, a slope, $k_1$, of the straight line $L_1$ is defined by the following expression (4):

$$k_1 = \{P_{ad}/(V_{ed}-V_0)\}/PEP \qquad (4)$$

A slope, $k_2$, of the straight line $L_2$ is obtained, as shown in FIG. 9, by dividing, by the ejection period ET, the difference, ($E_{es}$-$E_{ad}$), of the elastance E(t) at the end of the ejection period ET, i.e., the telesystolic elastance $E_{es}$, and the elastance $E_{ed}$ at the end of the pre-ejection period PEP. Since the telesystolic elastance $E_{es}$ is the slope of the telesystolic pressure-volume line $L_{es}$, the slope $k_2$ of the straight line $L_2$ is defined by the following expression (5):

$$k_2 = \{P_{max}/(V_{ed}-V_0) - P_{ad}/(V_{ed}-V_0)\}/ET \qquad (5)$$

Since "k" of the expression (2) is the ratio of the slope $k_2$ of the straight line $L_2$ to the slope $k_1$ of the straight line $L_1$, "k" is defined by the following expression (6):

$$k = \{(P_{max}-P_{ad})/P_{ad}\} \times (ET/PEP) \qquad (6)$$

FIG. 6 shows that the left-ventricle telesystolic elastance $E_{es}$ is defined by the following expression (7) and the aortic effective elastance $E_a$ is defined by the following expression (8), and therefore that the cardiac mechanical efficiency $E_{es}/E_a$ is defined by the following expression (9):

$$E_{es}=(P_{max}-P_{es})/(V_{ed}-V_{es}) \quad (7)$$

$$E_a=P_{es}/(V_{ed}-V_{es}) \quad (8)$$

$$E_{es}/E_a=(P_{max}-P_{es})/P_{es} \quad (9)$$

When $P_{max}$ which is defined by re-arranging the expression (6) is substituted for $P_{max}$ occurring to the expression (9), the expression (2) is obtained.

Figure 10:
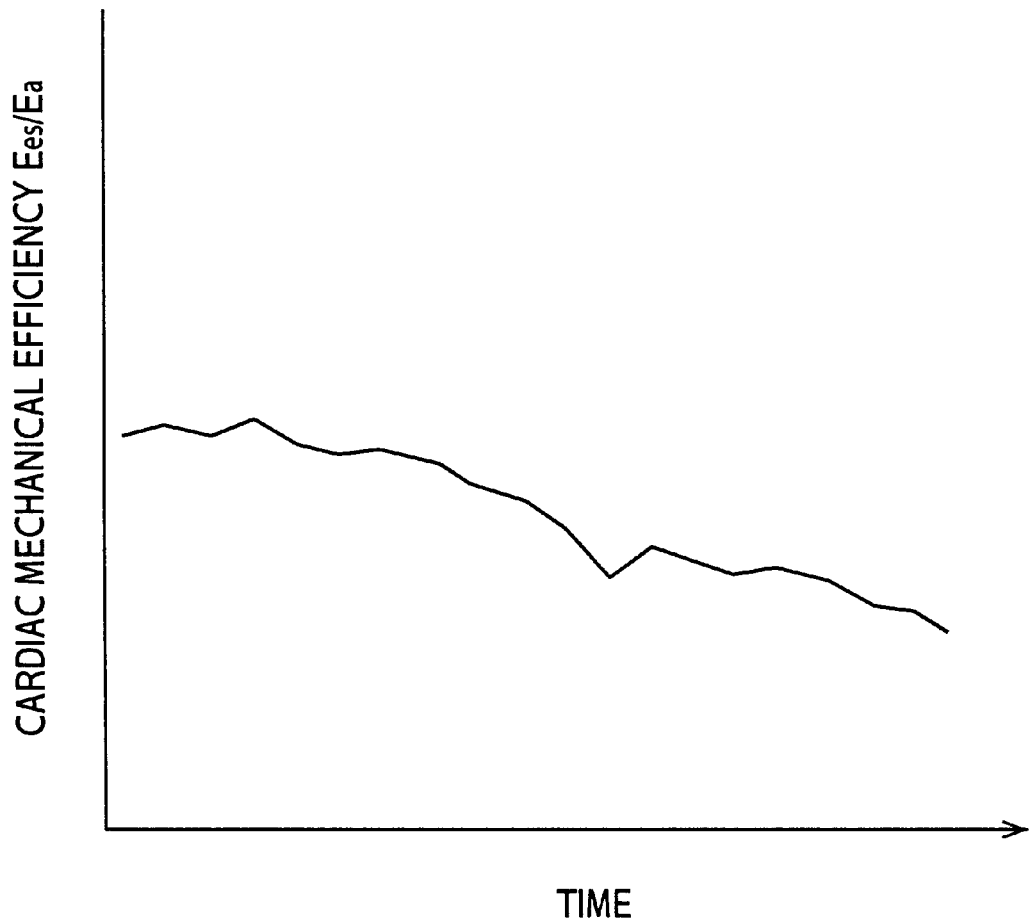
FIG. 10 is a graph showing a timewise change of cardiac mechanical efficiency values $E_{es}/E_a$ that is displayed on a display device of the apparatus of FIG. 1.

Back to FIG. 3, a display control means 98 controls the display device 32 to display a timewise trend of the cardiac mechanical efficiency values $E_{es}/E_a$ continuously determined by the means 88, as shown in FIG. 10. In the present embodiment, a greater value $E_{es}/E_a$ indicates a higher function of the heart of the patient.

Figure 11:
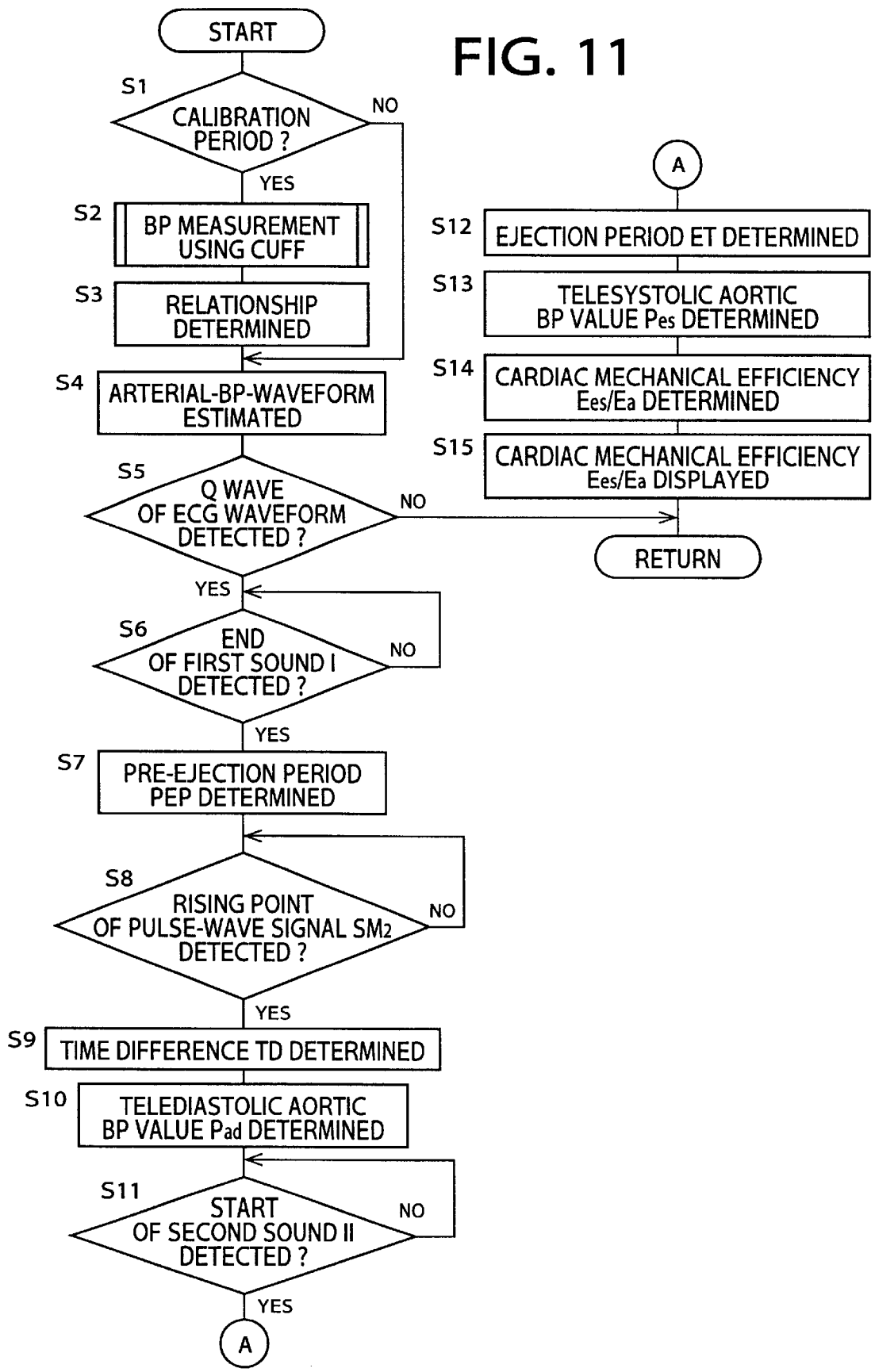
FIG. 11 is a flow chart representing a control program according to which the control device of FIG. 3 is operated.

Hereinafter, there will be described the operation of the present heart-function monitor apparatus 8 by reference to the flow chart of FIGS. 11.

First, at Step S1, the control device 28 judges whether a predetermined calibration period (e.g., twenty minutes) has elapsed. If a negative judgment is made at Step S1, the control of the control device 28 skips Step S2 and S3 and proceeds with Step S4 to estimate an arterial-BP waveform. On the other hand, if a positive judgment is made at Step S1, the control goes to Step S2 corresponding to the BP measuring means 76. At Step S2, the control device 28 carries out a BP measuring operation using the inflatable cuff 10, according to the oscillometric method or the Korotkoff-sound method. Step S2 is followed by Step S3 corresponding to the relationship determining means 78. At Step S3, the control device 28 determines a relationship, shown in FIG. 2, based on the BP values BP measured using the cuff 10 by the BP measuring means 76 and the magnitudes $P_M$ of the pressure pulse wave represented by the pulse-wave signal $SM_2$ detected by the active element of the pulse-wave sensor 46.

Step S3 is followed by Step S4 corresponding to the arterial-BP-waveform estimating means 80. At Step S4, the control device 28 converts, according to the relationship determined at Step S3, the pulse-wave signal SM2 detected by the active element of the pulse-wave sensor 46, into the estimated arterial-BP waveform BP(t), shown in FIG. 4, that represents actual BP values of the patient.

Step S4 is followed by Step S5 to judge whether the Q wave of the ECG waveform represented by the ECG signal SE has been detected. If a negative judgment is made at Step S5, the present control cycle is ended, and the next control cycle is started. On the other hand, if a positive judgment is made at Step S5, the control goes to Step S6 to judge whether the end of the first heart sound I represented by the heart-sound signal SS has been detected. If a negative judgment is made at Step S6, the control device 28 repeats Step S6. Meanwhile, if a positive judgment is made at Step S6, the control goes to Step S7 to determine, as the pre-ejection period PEP, a time period from the time of detection of the Q wave to the time of detection of the end of the first sound I. Thus, Steps S5 to S7 correspond to the PEP determining means 84.

At the following step, Step S8, the control device 28 judges, based on the pulse-wave signal $SM_2$ supplied from the pulse-wave sensor 46, whether the rising point of one heartbeat-synchronous pulse of the estimated arterial-BP waveform BP(t) has been detected. If a negative judgment is made at Step S8, the control device 28 repeats Step S8.

Meanwhile, if a positive judgment is made at Step S8, the control goes to Step S9 corresponding to the time-difference determining means 82. At Step S9, the control device 28 determines a time difference TD between the time when the end of the first sound I is detected at Step S6 and the time when the rising point of the pulse-wave signal $SM_2$ is detected at Step S8. This time difference TD means a propagation time needed for the blood ejected from the left ventricle of the heart to reach the radial artery 56 against which the pulse-wave sensor 46 is pressed.

At the following step, Step S10 corresponding to the telediastolic-aortic-BP determining means 92, the control device 28 determines, as the telediastolic aortic BP value $P_{ad}$, a BP value corresponding to a magnitude taken by the estimated arterial-BP waveform BP(t) at a time after the time difference TD determined at Step S9 from the time when the Q wave of the ECG waveform is detected at Step S5.

Step S10 is followed by Step S11 to judge whether the start of the second sound II represented by the heart-sound signal SS has been detected. The second sound II is produced when the the inner pressure of the left ventricle becomes not higher than that of the aorta and accordingly the aortic valve is closed. Therefore, the start of the second sound II means the end of contraction of the left ventricle, i.e., the telesystolic time. If a negative judgment is made at Step S11, the control device 28 repeats Step S11. Meanwhile, if a positive judgment is made at Step S11, the control goes to Step S12 to determine, as the ejection period ET during which the blood is ejected from the left ventricle, a time period from the time when the end of the firs sound I is detected at Step S6 to the time when the start of the second sound II is detected at Step S11. Thus, Steps S6, S11, and S12 correspond to the ET determining means 86.

At the following step, Step S13 corresponding to the telesystolic-aortic-BP determining means 90, the control device 28 determines, as the telesystolic aortic BP value $P_{es}$, a BP value corresponding to a magnitude taken by the estimated arterial-BP waveform BP(t) at a time after the time difference TD determined at Step S9 from the time when the start of the second sound II is detected at Step S11.

At the following step, Step S14 corresponding to the cardiac-mechanical-efficiency determining means 88, the control device 28 determines a cardiac mechanical efficiency $E_{es}/E_a$ by substituting the values $P_{ad}$, $P_{es}$, PEP, ET determined at Steps S7, S10, S12, S13, for the unknown quantities $P_{ad}$, $P_{es}$, PEP, ET of the expressions (2), (3).

Step S14 is followed by Step S15 corresponding to the display control means 98. At Step S15, the control device 28 controls the display device 28 to display the cardiac mechanical efficiency value $E_{es}/E_a$ determined at Step S14, in digits, and additionally display a trend graph, shown in FIG. 10, representing a timewise change of the continuously determined values $E_{es}/E_a$.

It emerges from the foregoing description that the cardiac-mechanical-efficiency determining means 88 (Step S14) determines, according to the predetermined relationship defined by the expression (2), the cardiac mechanical efficiency $E_{es}/E_a$ as the ratio of the left-ventricle telesystolic elastance $E_{es}$ to the aorta effective elastance $E_a$, based on the pre-ejection period PEP, the ejection period ET, the telediastolic aortic BP value $P_{ad}$, and the telesystolic aortic BP value $P_{es}$ all of which are non-invasively obtained. Thus, the present monitor apparatus 8 can non-invasively, continuously, and easily monitor the cardiac mechanical efficiency $E_{es}/E_a$ of the patient that corresponds to a cardiac function of the patient.

Figure 12:
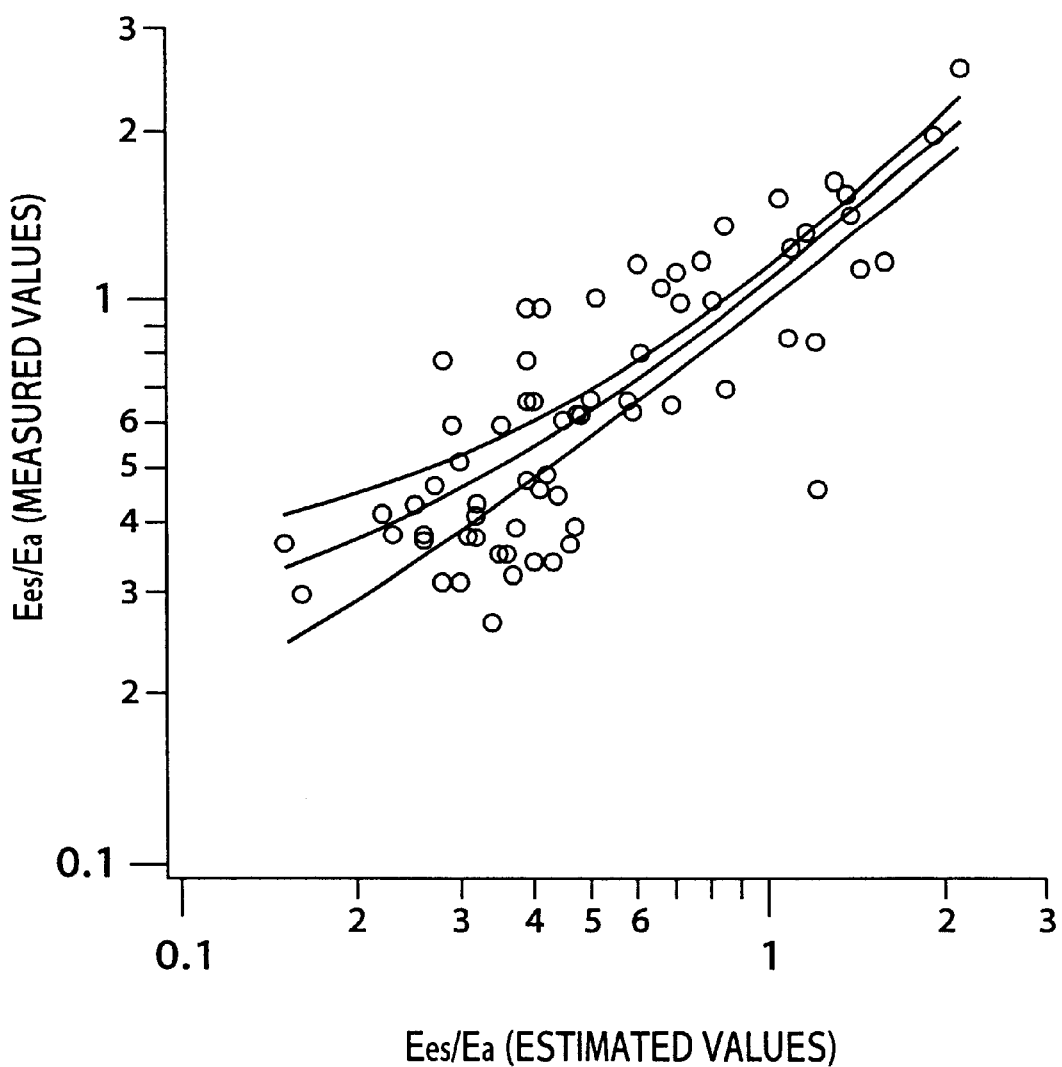
FIG. 12 is a graph showing a correlation between the cardiac mechanical efficiency values $E_{es}/E_a$ non-invasively calculated by the apparatus of FIG. 1, and cardiac mechanical efficiency values $E_{es}/E_a$ invasively measured.

FIG. 12 shows a correlation between the cardiac mechanical efficiency values $E_{es}/E_a$ non-invasively calculated or estimated by the monitor apparatus 8, and cardiac mechanical efficiency values $E_{es}/E_a$ actually measured by an invasive method. When the estimated cardiac mechanical efficiency $E_{es}/E_a$ shown in FIG. 12 is represented by "x" and the measured cardiac mechanical efficiency $E_{es}/E_a$ is represented by "y", a relationship between x and y is represented by the following expression (10):

$$y=0.96x+0.03 \ (r^2=0.9614, p<0.001) \tag{10}$$

Since mean square error is 0.1211, the cardiac mechanical efficiency values $E_{es}/E_a$ non-invasively estimated by the monitor apparatus 8, enjoy so high accuracy as to be practically used.

In the case where "k" occurring to the expression (2) is a variable defined as a function of the cardiac mechanical efficiency $E_{es}/E_a$ and the ratio (ET/PEP) of the ejection period ET to the pre-ejection period PEP, the cardiac-mechanical-efficiency determining means 88 can determine a more reliable cardiac mechanical efficiency $E_{es}/E_a$.

In the illustrated embodiment, the telediastolic-aorta-BP determining means 92 (Step S10) determines, as the telediastolic aorta BP value $P_{ad}$, a magnitude of the estimated arterial-BP waveform BP(t) that corresponds to an aorta BP value at the time when the Q wave of the ECG waveform is detected. Therefore, this means 92 can non-invasively and accurately determine the telediastolic aorta BP value $P_{ad}$.

In the illustrated embodiment, the telesystolic-aorta-BP determining means 90 (Step S13) determines, as the telesystolic aorta BP value $P_{es}$, a magnitude of the estimated arterial-BP waveform BP(t) that corresponds to an aorta BP value at the time when the start of the second heart sound II is detected. Therefore, this means 90 can non-invasively and accurately determine the telesystolic aorta BP value $P_{es}$.

In the illustrated embodiment, the PEP determining means 84 (Steps S5 to S7) determines, as the pre-ejection period PEP from the time when the contraction of the heart starts to the time when the ejection of blood actually starts, a time period from the time when the Q wave of the ECG waveform is detected through the ECG 68 to the time when the end of the first heart sound I is detected through the microphone 62. Thus, this means 84 can non-invasively and accurately determine the pre-ejection period PEP.

In the illustrated embodiment, the ET determining means 86 (Steps S6, S11 and S12) determines, as the ejection period ET, a time period from the time when the end of the first heart sound I is detected through the microphone 62, to the time when the start of the second sound II is detected. Thus, this means 86 can non-invasively and accurately determine the ejection period ET.

The present heart-function monitor apparatus 8 employs the display control means 98 (Step S15) which controls the display device 32 to display the cardiac mechanical efficiency values $E_{es}/E_a$ continuously determined by the means 88, along a time axis, as shown in FIG. 10. For example, in the case where the cardiac function of a patient who is undergoing a surgical operation is lowering, the present apparatus 8 can display a timewise change of the cardiac mechanical efficiency values $E_{es}/E_a$ that accurately reflects the lowering of the cardiac function. Thus, a medical staff such as a doctor or a nurse can estimate an abnormality of the cardiac function before the cardiac mechanical efficiency $E_{es}/E_a$ actually indicates an abnormal value.

While the present invention has been described in its preferred embodiments, it is to be understood that the invention may otherwise be embodied.

For example, in the illustrated embodiment, the telesystolic-aorta-BP determining means 90 determines, as the telesystolic aorta BP value $P_{es}$, a magnitude of the estimated arterial-BP waveform BP(t) at a time after the time difference TD from the time when the start of the second heart sound II is detected. The start of the second heart sound II may be replaced by the end of the T wave of the ECG waveform, as shown in FIG. 5. In addition, since the telesystolic aorta BP value $P_{es}$ can be approximated by a mean BP value (i.e., mean arterial pressure), MAP, according to a rule of thumb, an average of instantaneous BP values corresponding to one cycle or period, T, of the estimated arterial-BP waveform BP(t), that is, a mean BP value MAP may be used as the telesystolic aorta BP value $P_{es}$. Since the mean BP value MAP is defined as $\Sigma BP(t)/T$, it can be expressed by a BP value corresponding to a center of gravity of an area enveloped of the one cycle T of the estimated arterial-BP waveform BP(t).

In the illustrated embodiment, the telediastolic-aorta-BP determining means 92 determines, as the telediastolic aorta BP value Pad, a magnitude of the estimated arterial-BP waveform BP(t) at a time after the time difference TD from the time when the Q wave of the ECG waveform is detected. However, since the aortic pressure in the telediastolic period of the left ventricle does not change so largely for a considerably long time, as shown in FIG. 5, the estimated arterial-BP waveform BP(t) can be used to estimate an aortic pressure at an arbitrary point during a time period when the first sound I is detected, or an aortic pressure at the time when the R wave or S wave of the ECG waveform is detected, and determine the thus estimated aortic pressure as the telediastolic aorta BP value $P_{ad}$. Alternatively, a BP value corresponding to the rising point of each heartbeat-synchronous pulse of the estimated arterial-BP waveform BP(t) can be used as the telediastolic aorta BP value $P_{ad}$.

It is to be understood that the present invention may be embodied with other changes, improvements and modifications that may occur to those skilled in the art without departing from the scope and spirit of the invention defined in the appended claims.

What is claimed is:

1. An apparatus for monitoring a function of a heart of a living subject, comprising:

a pre-ejection period measuring device which non-invasively measures a pre-ejection period from a time when contraction of a cardiac muscle of a left ventricle of the heart starts, to a time when ejection of blood from the left ventricle starts;

an ejection-period measuring device which non-invasively measures an ejection period during which the blood is ejected from the left ventricle;

an aorta-pressure estimating means for estimating blood pressure values in an aorta of the subject;

a telediastolic-aorta-pressure determining means for determining, based on the aorta blood pressure values estimated by the aorta-pressure estimating means, a telediastolic blood pressure in the aorta at a telediastolic time of the heart;

a telesystolic-aorta-pressure determining means for determining, based on the aorta blood pressure values estimated by the aorta-pressure estimating means, a telesystolic blood pressure in the aorta at a telesystolic time of the heart; and a cardiac-mechanical-efficiency determining means for determining, based on the measured pre-ejection period, the measured ejection period, the determined telediastolic aorta blood pressure, and the determined telesystolic aorta blood pressure, a cardiac mechanical efficiency of the subject according a predetermined relationship between (A) cardiac mechanical efficiency and (B) (b1) pre-ejection period, (b2) ejection period, (b3) telediastolic aorta blood pressure and (b4) telesystolic aorta blood pressure.

2. An apparatus according to claim 1, wherein the predetermined relationship is defined by a following expression:

$$E_{es}/E_a = (P_{ad}/P_{es})\{1+k(ET/PEP)\}-1$$

where $E_{es}/E_a$ is the cardiac mechanical efficiency, $P_{ad}$ is the telediastolic aorta blood pressure, $P_{es}$ is the telesystolic aorta blood pressure, ET is the ejection period, PEP is the pre-ejection period, and k is a coefficient.

3. An apparatus according to claim 2, wherein the coefficient k of said expression is a variable expressed as a function of at least one of the cardiac mechanical efficiency and a ratio of the ejection period to the pre-ejection period.

4. An apparatus according to claim 2, wherein the coefficient k of said expression is a variable expressed as a function of the cardiac mechanical efficiency and a ratio of the ejection period to the pre-ejection period.

5. An apparatus according to claim 4, wherein the coefficient k of said expression is defined by a following expression:

$$k = a \times (E_{es}/E_a)^b + c \times (ET/PEP) + d$$

where a, b, c, and d are constants which are experimentally obtained.

6. An apparatus according to claim 1, wherein the pre-ejection period measuring device comprises:

an electrocardiograph which includes a plurality of electrodes adapted to contact a body surface of the subject, and which detects, from the subject, an electrocardiogram waveform including a Q wave;

a heart-sound detecting device which is located in a body cavity of the subject, at a position in a vicinity of the heart of the subject, and which detects, from the subject, a first heart sound I and a second heart sound II; and means for determining, as the pre-ejection period, a first time period from a time when the Q wave of the electrocardiogram waveform is detected to a time when an end of the first heart sound I is detected.

7. An apparatus according to claim 6, wherein the ejection-period measuring device comprises means for determining a second time period from the time when the Q wave of the electrocardiogram waveform is detected to a time when a start of the second heart sound II is detected, and determining, as the ejection period, a third time period obtained by subtracting the first time period from the second time period.

8. An apparatus according to claim 1, wherein the ejection-period measuring device comprises:

a heart-sound detecting device which is worn on the subject, at a position in a vicinity of the heart of the subject, and which detects, from the subject, a first heart sound I and a second heart sound II; and means for determining, as the ejection period, a time period from a time when an end of the first heart sound I is detected to a time when a start of the second heart sound II is detected.

9. An apparatus according to claim 1, wherein the ejection-period measuring device comprises means for determining, as the ejection period, a time period from a time of occurrence of a minimum point of a waveform representing the aorta blood pressure estimated by the aorta-blood-pressure estimating means to a time of occurrence of a notch of the waveform, the notch occurring at a time when an aortic valve of the heart is closed.

10. An apparatus according to claim 1, wherein the telediastolic-aorta-pressure determining means comprises:

an electrocardiograph which includes a plurality of electrodes adapted to contact a body surface of the subject, and which detects, from the subject, an electrocardiogram waveform including a Q wave; and means for determining, as the telediastolic aorta blood pressure, a blood pressure which is estimated by the aorta-pressure estimating means as an aorta blood pressure at a time when the Q wave of the electrocardiogram waveform is detected by the electrocardiograph.

11. An apparatus according to claim 1, wherein the telesystolic-aorta-pressure determining means comprises means for determining, as the telesystolic aorta blood pressure, a blood pressure which is estimated by the aorta-pressure estimating means as an aorta mean blood pressure.

12. An apparatus according to claim 1, wherein the telesystolic-aorta-pressure determining means comprises:

an electrocardiograph which includes a plurality of electrodes adapted to contact a body surface of the subject, and which detects, from the subject, an electrocardiogram waveform including a T wave; and means for determining, as the telesystolic aorta blood pressure, a blood pressure which is estimated by the aorta-pressure estimating means as an aorta blood pressure at a time when an end of the T wave of the electrocardiogram waveform is detected by the electrocardiograph.

13. An apparatus according to claim 1, wherein the telesystolic-aorta-pressure determining means comprises:

a heart-sound detecting device which is worn on the subject, at a position in a vicinity of the heart of the subject, and which detects at least a second heart sound II from the subject; and means for determining, as the telesystolic aorta blood pressure, a blood pressure which is estimated by the aorta-pressure estimating means as an aorta blood pressure at a time when a start of the second heart sound II is detected by the heart-sound detecting device.

14. An apparatus according to claim 1, wherein the pre-ejection period measuring device non-invasively measures, each time the heart contracts and expands, a pre-ejection period from a time when the contraction of the cardiac muscle of the left ventricle of the heart starts, to a time when the ejection of the blood from the left ventricle starts; the ejection period measuring device non-invasively measures, each time the heart contracts and expands, an ejection period during which the blood is ejected from the left ventricle starts; the aorta-pressure estimating means estimates, each time the heart contracts and expands, blood pressure values in the aorta of the subject; each time the heart contracts and expands, the telediastolic-aorta-pressure determining means determines, based on the estimated blood pressure values of the aorta, a telediastolic blood pressure in the aorta at a telediastolic time of the heart; each time the heart contracts and expands, the telesystolic-aortapressure determining means determines, based on the estimated blood pressure values of the aorta, a telesystolic blood pressure in the aorta at a telesystolic time of the heart; and, each time the heart contracts and expands, the cardiac-mechanical-efficiency determining means determines, based on the measured pre-ejection period, the measured ejection period, the determined telediastolic aorta blood pressure, and the determined telesystolic aorta blood pressure, a cardiac mechanical efficiency value of the subject according to the predetermined relationship between (A) cardiac mechanical efficiency and (B) (b1) pre-ejection period, (b2) ejection period, (b3) telediastolic aorta blood pressure and (b4) telesystolic aorta blood pressure, and wherein the apparatus further comprises a display device which displays, along an axis indicative of time, the cardiac mechanical efficiency values which are successively determined by the cardiac-mechanical-efficiency determining means as the heart successively contracts and expands.

15. An apparatus according to claim 1, wherein the aorta-pressure estimating means comprises:

a blood-pressure measuring device which includes an inflatable cuff adapted to be wound around a body portion of the subject, and which measures at least one blood pressure of the subject when an air pressure in the cuff is changed;

a pulse-wave sensor which is adapted to be pressed against an artery of the subject via a skin tissue of the subject so as to flatten a portion of a wall of the artery, and which detects a pressure pulse wave transmitted thereto from the artery via the flattened wall portion of the artery and the skin tissue;

relationship determining means for determining a relationship between blood pressure and pressure-pulse-wave magnitude, based on at least one blood pressure measured by the blood-pressure measuring device and at least one magnitude of the pressure pulse wave detected by the pulse-wave sensor; and means for calibrating, according to the determined relationship, instantaneous magnitudes of the pressure pulse wave detected by the pulse-wave sensor, and thereby providing a waveform representing the estimated aorta blood pressure values of the subject.

* * * * *